United States Patent [19]

Smith et al.

[11] Patent Number: 5,955,374
[45] Date of Patent: Sep. 21, 1999

[54] METHOD OF DETECTION OF BILIRUBIN IN URINE ON AN AUTOMATED ANALYZER

[76] Inventors: Jack V. Smith, 8505 42nd Ave. N., St. Petersburg, Fla. 33709; Jesse M. Carter, 910 S. Rome Ave., Tampa, Fla. 33606

[21] Appl. No.: 08/591,959

[22] Filed: Jan. 29, 1996

Related U.S. Application Data

[63] Continuation-in-part of application No. 08/347,123, Nov. 23, 1994, abandoned.

[51] Int. Cl.$^6$ ................................................ G01N 33/00
[52] U.S. Cl. ............................. 436/97; 436/12; 436/43; 436/164; 422/68.1
[58] Field of Search ................................ 436/12, 43, 63, 436/97, 164, 171, 175, 176; 422/63, 67, 68.1, 82.05, 82.09

[56] References Cited

U.S. PATENT DOCUMENTS

| | | | |
|---|---|---|---|
| 3,754,862 | 8/1973 | Wahlefeld et al. | 436/97 |
| 3,853,476 | 12/1974 | Rittersdorf et al. | 436/97 |
| 3,880,588 | 4/1975 | Rittersdorf et al. | 436/97 |
| 3,923,459 | 12/1975 | Ertingshausen et al. | 436/97 |
| 4,038,031 | 7/1977 | Lam | 436/97 |
| 4,404,286 | 9/1983 | Shull | 436/97 |
| 4,672,041 | 6/1987 | Jain | 436/97 |
| 4,683,208 | 7/1987 | Aoyama et al. | 436/12 |
| 5,112,769 | 5/1992 | Modrovich | 436/97 |
| 5,149,272 | 9/1992 | Wu et al. | 436/97 |

*Primary Examiner*—Maureen M. Wallenhorst

[57] ABSTRACT

Method for detecting total bilirubin in urine using a chemical detection means with an indicator that will produce a detectable quantitative response in the presence of bilirubin in urine on an automated analyzer.

9 Claims, No Drawings

METHOD OF DETECTION OF BILIRUBIN IN URINE ON AN AUTOMATED ANALYZER

PRIOR APPLICATIONS

This application is a continuation in part of application Ser. No. 08/347,123, filed Nov. 23, 1994, now abandoned.

BACKGROUND OF THE INVENTION

The present invention is concerned with an improved diagnostic agent for the rapid and sensitive detection of total bilirubin in body fluids, particularly in urine.

The detection of bilirubin is of great importance in the diagnosis of disease of the liver and gall bladder. Bilirubin, a highly pigmented yellow compound, is a degradation product of hemoglobin. The appearance of direct and indirect (total) bilirubin in the urine can provide an early indication of liver disease and is often detected long before the development of jaundice. Bilirubin provides early detection of hepatitis, cirrhosis, gallbladder disease, and cancer, and should be included in every routine urinalysis. 1

1. Strasinger, S. K.: Urinalysis and Body Fluids. F. A. Davis, Philadelphia, 1994.

Methods for the detection of bilirubin in the urine have been known for a long time. Historically, methods are dependent upon the evaluation of the colored compounds formed by the coupling of bilirubin with diazonium salts. For this purpose, diazosulfanilic acid, 2,4-dichloroaniline diazonium salt, 2,6-dichlorobenzene-diazonium-tetrafluoroborate, and p-nitrobenzene-diazonium-p-toulenesulfonate in an acid medium have previously been most used.

SUMMARY OF THE INVENTION

Recently, in medical practice and in clinical laboratories, the so-called "rapid test" has been used more and more as a diagnostic aid. These simple devices, usually test papers (called reagent strips or dipsticks), which permit detection or semi-quantitative determination of pathological components of the body in a rapid and certain manner, even by untrained personnel, such as medical auxiliaries. However, reagent strip color reactions for bilirubin are more difficult to interpret than other test reactions (liquid chemistry) and are easily influenced by other pigments present in the urine. Atypical color reactions are frequently noted on visual examination as well as by automated strip readers. Further testing should be performed, because of these interferences inherent in the dipstick's technology. 1

1. Strasinger, S. K.: Urinalysis and Body Fluids. F. A. Davis, Philadelphia, 1994.

Although many attempts have been made to modify the various qualitative methods, up till now an acceptable quantitative method has not been developed for routine laboratory use. 2

2. Tietz, N. W.: Fundamentals of Clinical Chemistry, W. B. Saunders, Philadelpia, 1976.

Thus, for example, German Pat. No. 1,102,444 describes a reagent tablet containing a diazonium salt and a strong acid which is placed on a spot plate moistened with a body fluid and, after moistening with water, makes the bilirubin visible as a violet ring on the substrate. It is obvious this diagnostic agent is too laborious for general use. For wide applicability in medical practices and hospitals it is, however, desirable to make available an automated test that can be performed on a preprogrammed analyzer at a specified wavelength, thus relieving laboratorians of subjective interpretation of this health related data, and provide accurate quantitative results. This purpose is best fulfilled by this new invention, a liquid reagent system designed specifically for autoanalyzer use.

It is known from German Patent No. 2,007,013, U.S. Pat. No. 3,880,588, and U.S. Pat. No. 3,853,476 the use of test papers which contain diazonium salts for the detection of bilirubin in urine. However, these methods are relatively insensitive (and qualitative), and also suffer from disadvantages with regard to the speed of the reaction(s) and their sensitivity and selectivity. These three disadvantages decrease their practical utility. For example, urobilinogen which is present in urine also reacts with these formulations resulting in falsely elevated bilirubin values. Furthermore, other normal components of the urine matrix can also cross-react with these formulations yielding falsely elevated values.

In U.S. Pat. No. 5,112,769, Modrovich teaches a bilirubin method that determines direct bilirubin not total bilirubin (as the present device does). For urinary bilirubin determination of total bilirubin quantitation is of the utmost importance. Furthermore, Modrovich teaches the inclusion of an aromatic sulfate (sulfosalicylic) to catalize the reaction and stabilize his diazo compound. The present device does not require this addition in order to achieve similar stability and reactivity. In addition, Modrovich teaches a method designed for whole blood and serum, not for urine. Distinct and numerous differences and problems are presented by these two unique matrices to the analytical process.

DESCRIPTION OF THE INVENTION

We have, surprisingly, discovered that employing specific diazonium salts in an aqueous medium (liquid) as indicators of total bilirubin in combination with compounds to buffer and enhance reagent stability, and activators to increases sensitivity to the desired level for accurate and clinically significant measurement of total urine bilirubin, the previously mentioned difficulties are overcome.

The diazonium salts used in this invention can be prepared from known aromatic amines by diazotization. The diazonium salts are preferably used in the form of fluoborates, whose stability is well known; however, other stable salts including such as aryl-sulfonates (i.e. naphthalene-1,5-disulfonates) can also be used. Indicators other than diazonium salts can be used that will give a measurable response in the presence of bilirubin.

Activators that can be effectively utilized for the purpose of this invention include cationic, anionic, and non-ionic wetting agents, and phosphoric acid diester compounds (such as Diphenyl Phosphate).

Compounds to buffer and stabilize this single bilirubin reagent include Metaphosphoric Acid and Citric Acid used in combination to form an acid-buffer complex that both stabilizes and buffers the reagent simultaneously, while allowing inclusion of the indicator and activator in the same solution without color development occurring in the absence of bilirubin. Note, formulas described in all the prior patents excluding the formula of U.S. Pat. No. 5,112,769 are unstable. The claimed stability of U.S. Pat. No. 5,112,769 is from the use of sulfated diazonium salts.

Wetting agents can also improve fluid flow dynamics, reduce the need for degassing the reagent, activate color development as well as inflection point of color, among other attributes.

Furthermore, this automated liquid reagent system is carrier-free and does not require filter paper or absorbent carriers (i.e., dipsticks) which all of the prior art except Modrovich cite as essential. In addition, the present art has no need of organic solvents such as ethyl acetate or chloroform, while much of the prior art includes as essential.

It can further be noted that use of these solvents would be detrimental to an autoanalyzer's sampling and photometric mechanisms (cuvettes) which are primarily plastic.

Also, the present invention provides a means for the detection of total bilirubin (direct and indirect bilirubin) in urine, which contains at least one diazonium salt and acid sufficient for the coupling reaction between the bilirubin and the diazonium salt to occur. Organic and inorganic acids can be used for this purpose. Of particular utility are oxalic acid, citric acid, potassium bisulfate and, metaphosphoric acid. In addition, metaphosphoric acid's provide stability to the diazo indicator salt.

The automated reagent according to the present invention reacts with bilirubin-containing urine in 1 to 30 seconds to form a detectable color in the ultraviolet and/or visible wavelength range from 340 to 700 nanometers. The detection of serum bilirubin is of course, also possible using this automated reagent according to the present invention.

The following Examples are given for the purpose of illustrating the present invention:

EXAMPLE I

Liquid reagent is successfully compounded by dissolving the following chemicals at room temperature (25 degree C):

Solution I (R1):

| | |
|---|---|
| p-nitrobenzene-diazonium-p-toluenesulfonate | 0.10 g |
| sodium carbonate | 1.0 g |
| boric acid | 3.0 g |
| Phosphoric acid diphenyl ester 5.0 g | 5.0 g |
| Propanol | 10.0 ml |
| dodecyl-benzene-sulfonic acid sodium salt | 0.4 g |
| distilled water add to | 100.0 ml |

Instrument parameters (Hitachi 717):

CHEMISTRY PARAMETERS

| | |
|---|---|
| TEST | [URINE BILI] |
| ASSAY CODE | [1 POINT]:[0]-[50] |
| SAMPLE VOLUME | [10] |
| R1 VOLUME | [300] [100] [NO] |
| R2 VOLUME | [0] [100] [NO] |
| WAVE LENGTH | [700] [415] |
| CALIB. METHOD | [LINEAR] [0] [0] |
| STD. (1) CONC. -POS. | [0]-[1] |
| STD. (2) CONC. -POS. | [1.0]-[2] |
| STD. (3) CONC. -POS. | [0]-[0] |
| STD. (4) CONC. -POS. | [0]-[0] |
| STD. (5) CONC. -POS. | [0]-[0] |
| STD. (6) CONC. -POS. | [0]-[0] |
| SD LIMIT | [999] |
| DUPLICATE LIMIT | [32000] |
| SENSITIVITY LIMIT | [0] |
| ABS. LIMIT (INC/DEC) | [32000] [INCREASE] |
| PROZONE LIMIT | [0] [UPPER] |
| EXPECTED VALUE | [0]-[1.0] |
| TECH. LIMIT | [0]-[100] |
| INSTRUMENT FACTOR | [1.0] |

A sample of bilirubin-containing urine is obtained which, upon mixing with the liquid reagent (R1) on the autoanalyzer which has preset parameters, gives a measurable response after 1 to 600 seconds. This method for detecting total bilirubin in a patient's urine comprises placing an aliquot of the urine to be tested in an automated analyzer sampling cup, placing the cup in a sampling tray within the automated analyzer, transferring the urine to a cuvette mounted within the automated analyzer, injecting one or more reagent compositions in an aqueous medium into the cuvette, the reagent compositions containing a buffer to adjust the pH of the urine to an acidic value and stabilize the single instant reagent, an activating compound that aids in the coupling reaction between bilirubin and diazonium[s] salts, a surfactant to decrease surface tension and promote mixing on a molecular level and activate the reaction, and color developer consisting of a diazonium salt or salts capable of coupling with bilirubin (direct or indirect) or a bilirubin indicator compound capable of giving a detectable response in the presence of total bilirubin, an amount of an acid sufficient for the coupling reaction, and a stabilizing agent to prevent color development and stabilize the diazonium salts without the presence of bilirubin in urine, reading urine and standards after mixing with reagent at specified intervals, in accordance with a preprogrammed code introduced into the automated analyzer, at a preprogrammed monochromatically specified wavelength of the analyzer's spectrophotometer, to compare absorbance of the patient's urine and reagent composition complex with that of a standard containing a known concentration of bilirubin and thereby determining the presence or absence of total bilirubin in the patient's urine. The limit of sensitivity is about 0.010 to 1.000 mg/dl.

EXAMPLE II

Liquid reagents are successfully compounded by dissolving the following chemicals at room temperature (25 degree C):

Solution I (R1):

| | |
|---|---|
| 2,6-dichlorobenzene-diazonium-tetrafluoroboarte | 0.10 g |
| metaphosphoric acid | 10.0 g |
| citric acid | 1.0 g |
| distilled water add to | 100.0 ml |

Solution II (R2):

| | |
|---|---|
| Phosphoric acid diphenyl ester 5.0 g | 5.0 g |
| methanol | 10.0 ml |
| sodium dodecyl sulfate | 0.1 g |
| distilled water add to | 100.0 ml |

Instrument parameters (Hitachi 717):

CHEMISTRY PARAMETERS

| | |
|---|---|
| TEST | [URINE BILI] |
| ASSAY CODE | [1 POINT]:[0]-[50] |
| SAMPLE VOLUME | [10] |
| R1 VOLUME | [125] [100] [NO] |
| R2 VOLUME | [125] [100] [NO] |
| WAVE LENGTH | [700] [415] |
| CALIB. METHOD | [LINEAR] [0] [0] |
| STD. (1) CONC. -POS. | [0]-[1] |
| STD. (2) CONC. -POS. | [1.0]-[2] |
| STD. (3) CONC. -POS. | [0]-[0] |
| STD. (4) CONC. -POS. | [0]-[0] |
| STD. (5) CONC. -POS. | [0]-[0] |
| STD. (6) CONC. -POS. | [0]-[0] |
| SD LIMIT | [999] |
| DUPLICATE LIMIT | [32000] |
| SENSITIVITY LIMIT | [0] |
| ABS. LIMIT (INC/DEC) | [32000] [INCREASE] |
| PROZONE LIMIT | [0] [UPPER] |
| EXPECTED VALUE | [0]-[1.0] |
| TECH. LIMIT | [0]-[100] |
| INSTRUMENT FACTOR | [1.0] |

A sample of bilirubin-containing urine is obtained which, upon mixing with the liquid reagent (R1) on the autoanalyzer with preset parameters, the solution containing both urine and R1 are then mixed with the liquid reagent R2 which gives a measurable response after 1 to 600 seconds. The limit of sensitivity is about 0.010 to 1.000 mg/dl. This method for detecting total bilirubin in a patient's urine comprises placing an aliquot of the urine to be tested in an automated analyzer sampling cup, placing the cup in a sampling tray within the automated analyzer, transferring the urine to a cuvette mounted within the automated analyzer, injecting one or more reagent compositions in an aqueous medium into the cuvette, the reagent compositions containing a buffer to adjust the pH of the urine to a acidic value and stabilize the instant reagent, an activating compound that aids in the coupling reaction between bilirubin and diazonium[s] salts, a surfactant to decrease surface tension and promote mixing on a molecular level and activate the reaction, and color developer consisting of a diazonium salt or salts capable of coupling with bilirubin (direct or indirect) or a bilirubin indicator compound capable of giving a detectable response in the presence of total bilirubin, an amount of an acid sufficient for the coupling reaction, and a stabilizing reagent to prevent color development and stabilize the diazonium salts without the presence of bilirubin in urine, reading urine and standards after mixing with reagents at specified intervals, in accordance with a preprogrammed code introduced into the automated analyzer, at a preprogrammed monochromatically specified wavelength of the analyzer's spectrophotometer, to compare absorbance of the patient's urine and reagent composition complex with that of a standard containing a known concentration of bilirubin and thereby determining the presence or absence of total bilirubin in the patient's urine. The limit of sensitivity is about 0.010 to 1.000 mg/dl.

EXAMPLE III

Liquid reagent is successfully compounded by dissolving the following chemicals at room temperature (25 degree C):

Solution I (R1):

| | |
|---|---|
| 3,5 Dichlorophenyl diazonium tetrafuoroborate | 2.6 mg |
| Metaphosphoric Acid | 7.5 g |
| Citric Acid | 3.0 g |
| Dodecylbenzenesulfonic Acid, Sodium Salt | 0.4 g |
| Diphenyl Phosphate | 0.5 g |
| Isopropanol | 1.0 ml |
| distilled water add to | 100.0 ml |

Instrument parameters (Hitachi 717):

CHEMISTRY PARAMETERS

| | |
|---|---|
| TEST | [URINE BILI] |
| ASSAY CODE | [1 POINT]:[0]–[50] |
| SAMPLE VOLUME | [10] |
| R1 VOLUME | [300] [100] [NO] |
| R2 VOLUME | [0] [100] [NO] |
| WAVE LENGTH | [700] [415] |
| CALIB. METHOD | [LINEAR] [0] [0] |
| STD. (1) CONC. -POS. | [0]–[1] |
| STD. (2) CONC. -POS. | [1.0]–[2] |
| STD. (3) CONC. -POS. | [0]–[0] |
| STD. (4) CONC. -POS. | [0]–[0] |
| STD. (5) CONC. -POS. | [0]–[0] |
| STD. (6) CONC. -POS. | [0]–[0] |
| SD LIMIT | [999] |
| DUPLICATE LIMIT | [32000] |
| SENSITIVITY LIMIT | [0] |
| ABS. LIMIT (INC/DEC) | [32000] [INCREASE] |
| PROZONE LIMIT | [0] [UPPER] |
| EXPECTED VALUE | [0]–[1.0] |
| TECH. LIMIT | [0]–[100] |
| INSTRUMENT FACTOR | [1.0] |

A sample of bilirubin-containing urine is obtained which, upon mixing with the liquid reagent (R1) on the autoanalyzer which has preset parameters, gives a measurable response after 1 to 600 seconds. The limit of sensitivity is about 0.010 to 1.000 mg/dl. It should be stressed that no prior art (patents) including U.S. Pat. Nos. 3,754,862, 3,853,466, 3,880,588, 3,853,476, 5,149,272, 4,683,208, 4,672,041, 4,404,286, 4,038,031, 3,923,459, and 5,112,769 have cited, taught, or envisioned the use of 3,5 Dichlorophenyl diazonium tetrafuoroborate as a substrate for the use of analyzing bilirubin in urine on an automated analyzer with the unique formulation of EXAMPLE III. This substrate in the presence of the novel acid-buffer complex has the unique characteristics of long term stability, superior sensitivity, and resistance to urinary matrix interference that is a marked advancement in the art of bilirubin analysis. The present invention includes diphenyl phosphate to activate and accelerate the diazo-bilirubin coupling reaction which produces a colored product. Other diphenyl and diphenyl-ester compounds can be utilized to produce the same effects. In addition, isopropanol is added to effect solubilization of the diphenyl compound with the invention's aqueous medium. Other short chain alkyl or aryl organic alcohols may be substituted for isopropanol.

The following is an example of a method for analyzing urine bilirubin on an automated instrument. First place an aliquot of the urine to be tested in an automated analyzer sampling cup, then place the cup in a sampling tray within the automated analyzer, transferring the urine to a cuvette mounted within the automated analyzer, injecting one or more reagent compositions in an aqueous medium into the cuvette, the reagent compositions containing an acid-buffer complex to adjust the pH of the urine to an acidic state while stabilizing the reagent to prevent color development of the diazonium salts without the presence of bilirubin in urine, an activating compound that aids in the coupling reaction between bilirubin and diazonium salts, a surfactant to decrease surface tension and promote mixing on a molecular level and activate the reaction, and color developer consisting of a diazonium salt or salts capable of coupling with bilirubin, or a bilirubin indicator compound capable of giving a detectable response in the presence of bilirubin, an amount of an acid sufficient for the coupling reaction to take place, reading urine, serum, plasma, blood, and standards after mixing with reagents at specified intervals, in accordance with a preprogrammed code introduced into the automated analyzer (see EXAMPLE I page 6 instrument parameters), at a preprogrammed monochromatically specified wavelength of the analyzer's spectrophotometer, to compare absorbance of the patient's urine and reagent composition complex with that of a standard containing a known concentration of bilirubin and thereby quantitatively determine the presence or absence of bilirubin in the patient's urine. This device (method) can use a single (combined), or two-part reagent composition in an aqueous medium injected into the reaction cuvette as illustrated by EXAMPLES I or II. The two-reagent system could not be combined to form a single reagent system without inventive modifications. This device's (method's) wavelength of choice can vary from about 340 to 700 nanometers. Finally, this device's (method's) means of detecting total bilirubin in body fluids, comprises contacting a test sample or urine, serum, or standard suspected of containing bilirubin with a reagent composition to detect bilirubin as illustrated in EXAMPLE 3. The following is a distillation of the afore mentioned. A method for detecting total bilirubin in urine comprises placing an aliquot of the urine to be tested in an automated analyzer sampling cup, placing the cup in a sampling tray within the automated analyzer, transferring the urine to a cuvette mounted within the automated analyzer, injecting a single reagent composition in an aqueous medium into the cuvette, the reagent composition containing an acid-buffer complex to adjust the pH of the urine to an acidic value and stabilize the single reagent to prevent color development of diazonium salts without the presence of bilirubin in urine, an activating compound that aids in the coupling reaction between bilirubin and diazonium salts, a surfactant to decrease surface tension and promote mixing on a molecular level and activate the reaction, and color developer consisting of a diazonium salt or salts capable of coupling with direct and indirect bilirubin or a bilirubin indicator compound capable of giving a detectable response in the presence of bilirubin, and an amount of an acid sufficient for the coupling reaction, reading urine and standards after mixing with and reagents at specified intervals, in accordance with a preprogrammed code introduced into the automated analyzer, at a preprogrammed monochromatically specified wavelength, to compare absorbance of the patient's urine and reagent composition complex with that of a standard containing a known concentration of bilirubin and thereby determining the presence or absence of total bilirubin in the patient's urine. The wavelength of the analyzer's spectrophotometer is about 340 to 700 namometers, and the specific single reagent formulation for detecting total bilirubin in body fluids, which includes contacting a test sample comprised of urine or serum suspected of containing bilirubin, or bilirubin standard (containing a known amount of bilirubin) with a reagent composition comprising: 3,5 Dichlorophenyl diazonium tetrafluoroborate, Metaphosphoric Acid, Citric Acid, Dodecylbenzenesulfonic Acid Sodium Salt, Diphenyl Phosphate, and Isopropanol.

It will be understood that the specification and examples are illustrative but not limitative of the present invention and that other embodiments within the spirit and scope of the invention will suggest themselves to those skilled in the art.

What is claimed is:

1. A method for detecting total bilirubin in a test sample of urine comprising the steps of:

A.) placing aliquots of a test sample of urine and a standard to be tested in automated analyzer sampling cups, B.) placing the cups in a sampling tray within an automated analyzer, transferring the aliquots of urine and standard to cuvettes mounted within the automated analyzer, injecting a single reagent composition in an aqueous medium into the cuvettes, the single reagent composition comprising the following components: a color developer consisting of a diazonium salt or salts that couple with direct and indirect bilirubin or a bilirubin indicator compound capable of giving a detectable response in the presence of bilirubin, an acid-buffer complex to adjust the pH of the urine to an acidic value and to prevent color development of the color developer without the presence of bilirubin in urine, an activating agent, a surfactant to decrease surface tension, promote mixing on a molecular level and activate color development in the presence of bilirubin in urine, and an acid, and C.) reading absorbance values for the aliquots of urine and standard at specified intervals, in accordance with a preprogrammed code introduced into the automated analyzer, at a preprogrammed monochromatically specified wavelength, to compare absorbance of the single reagent composition plus the test sample of urine with that of the single reagent composition plus the standard containing a known reference concentration of bilirubin and thereby determining the concentration of bilirubin in the test sample of urine.

2. The method according to claim 1 wherein the components of the single reagent composition can be split apart into a two reagent composition that contains the same components of the single reagent composition of claim 1 and when combined can detect total bilirubin in urine.

3. The method according to claim 1 wherein the wavelength of the automated analyzer is about 340 to 700 nanometers.

4. The method according to claim 1 wherein the activating compound is Diphenyl Phosphate, Diphenyl, or Diphenyl ester compounds.

5. The method according to claim 1 wherein the acid-buffer complex is made from organic or inorganic acids.

6. The method according to claim 1 wherein the surfactant is anionic, cationic, or non-ionic.

7. The method according to claim 1 wherein the single reagent composition contains an organic alcohol to aid in solubilization of the activating compound.

8. The method according to claim 7 wherein the organic alcohol is any short chain alkyl or aryl organic alcohol.

9. Method for detecting total bilirubin in urine, which comprises the steps of contacting a test sample of urine suspected of containing bilirubin with an aqueous reagent composition comprising: 3,5 Dichlorophenyl diazonium tetrafluoroborate, Metaphosphoric Acid, Citric Acid, Dodecylbenzenesulfonic Acid Sodium Salt, Diphenyl Phosphate, and Isopropanol.

* * * * *